US00PP15734P2

(12) United States Plant Patent
Rodriquez

(10) Patent No.: US PP15,734 P2
(45) Date of Patent: Apr. 26, 2005

(54) ***DRACAENA* PLANT NAMED 'NORJIM'**

(50) Latin Name: *Dracaena marginata*
Varietal Denomination: Norjim

(75) Inventor: Norman Alfredo Jimenez Rodriquez, Alajuela (CR)

(73) Assignee: Las Palmas International Trade B.V., Aalsmeer (NL)

( * ) Notice: Subject to any disclaimer, the term of this patent is extended or adjusted under 35 U.S.C. 154(b) by 28 days.

(21) Appl. No.: 10/795,674

(22) Filed: Mar. 8, 2004

(51) Int. Cl.[7] ..... A01H 5/00
(52) U.S. Cl. ..... Plt./383
(58) Field of Search ..... Plt./383

*Primary Examiner*—Anne Marie Grunberg
*Assistant Examiner*—June Hwu
(74) *Attorney, Agent, or Firm*—Mark P. Bourgeois

(57) ABSTRACT

A new cultivar of *Dracaena* plant named 'Norjim' that is characterized by variegated leaves with yellow-green center stripes and grey-red margins, strong leaves having an ensiform shape and good resistance during the rainy season to bacterial growth. In combination, these traits set 'Norjim' apart from all other known existing varieties of *Dracaena*.

1 Drawing Sheet

Botanical classification: *Dracaena marginata.*
Variety denomination: 'Norjim'.

BACKGROUND OF THE INVENTION

The present invention relates to a new and distinct cultivar of *Dracaena* plant botanically known as *Dracaena marginata* and hereinafter referred to by the cultivar name 'Norjim'.

The new cultivar was discovered in January of 2001 by the inventor in a cultivated area of Calle Jimenez, La Tigra, San Carlos, Costa Rica. 'Norjim' was discovered as a naturally occurring mutation of an unnamed plant of *Dracaena marginata* (not patented).

Asexual reproduction of the new cultivar 'Norjim' occurred when cuttings were propagated. The first reproduction was in June of 2001 in Calle Jimenez, La Tigra, San Carlos, Costa Rica.

Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Dracaena* cultivar 'Norjim'. These traits in combination distinguish 'Norjim' as a new and distinct cultivar apart from all other existing varieties of *Dracaena* known to the inventor.

1. *Dracaena* 'Norjim' exhibits variegated leaves with yellow-green center stripes and grey-red margins.
2. *Dracaena* 'Norjim' exhibits strong leaves.
3. *Dracaena* 'Norjim' exhibits leaves with an ensiform shape.
4. *Dracaena* 'Norjim' exhibits resistance during the rainy season to bacterial growth.

The closest comparison plant is the parent plant an unnamed *Dracaena marginata.*

The new cultivar 'Norjim' is distinguishable from the parent *Dracaena,* by the following characteristics:

1. 'Norjim' has yellow stripes in the leaf center, the leaves of the parent plant are all green.
2. 'Norjim' has good resistance during the rainy season to bacterial growth.

BRIEF DESCRIPTION OF THE DRAWING

The accompanying photograph illustrates the distinguishing traits of *Dracaena* 'Norjim'. The plant in the photograph shows an overall view of a 6 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Dracaena* cultivar named 'Norjim'. Data was collected in Boskoop, The Netherlands from plants grown in Calle Jimenez, La Tigra, San Carlos, Costa Rica. The plants were 6 week old outdoor grown plants in 11 cm diameter containers. The time of year was Winter. The temperature ranged from 12 to 32° Centigrade. The light level was natural outdoor light and there were no photoperiodic treatments or growth retardants used. Color determinations are in accordance with The Royal Horticultural Society Colour Chart 2001 edition, except where general color terms of ordinary dictionary significance are used. The growing requirements are similar to the species. 'Norjim' has not been tested under all possible conditions and phenotypic differences may be observed with variations in environmental, climatic, and cultural conditions, however, without any variance in genotype.

Botanical classification: *Dracaena marginata* 'Norjim'.
Parentage: 'Norjim' is a branch sport of an unnamed *Dracaena marginata.*
Annual or perennial: Perennial.
Use: Ornamental.
Vigor: Moderate.
Growth habit: Upright.
Plant shape: Inverted triangle.

Suitable container size: 17 cm container.
Height: 50 cm in height.
Width: 81 cm in width.
Hardiness: USDA Zone 10.
Growth rate: Approximately 8 cm. per month.
Propagation: Cuttings.
Time to initiate roots: Approximately 21 days to produce roots on an initial cutting.
Time to produce a rooted cutting or liner: Approximately 35 days.
Root system: Fine and fibrous.
Root color: Orange brown 175A to 175B.
Stem:
*Branching habit.*—Lateral branches grow from thick main stems after pruning.
*Average number of lateral branches.*—1.
*Lateral branch diameter.*—1.5 cm. in diameter.
*Stem strength.*—Very strong.
*Stem color.*—137A and 150B to varies from 154B to 154D and 186C.
*Stem pubescence.*—Absent.
*Internode length.*—4.0 mm.
*Stem shape.*—Round.
*Stem surface.*—Dull, smooth, leaf scars visible on stems.
Foliage:
*Texture.*—Smooth, glossy, slightly leatherly.
*Leaf arrangement.*—Alternate.
*Compound or single.*—Single.
*Quantity of leaves per lateral branch.*—33.
*Leaf shape.*—Ensiform.
*Leaf apex.*—Acuminate.
*Leaf base.*—Sheating.
*Leaf length.*—43.4 cm. in length.
*Leaf width.*—1.9 cm. in width.
*Pubescence.*—Absent.
*Leaf margin.*—Entire.
*Vein pattern.*—Parallel.
*Young leaf color* (*lower surface*).—Green 143A with 3 to 6 yellow-green center stripes 144B to 144D along the length of the leaf that are 1 mm to 4 mm wide and margins grey-red that vary from 178A to 178B and that are 1 mm wide.
*Young leaf color* (*upper surface*).—Green 139A to 147A with 3 to 6 yellow-green center stripes 144B along the length of the leaf that are 1 mm to 4 mm wide and margins grey-red that vary from 178A to 178B and that are 1 mm wide.
*Mature leaf color* (*lower surface*).—Green 137A with 3 to 6 yellow-green center stripes that vary from 150B to 154B to 154D along the length of the leaf that are 1 mm to 4 mm wide and margins grey-red 186C that are 1.5 mm wide.
*Mature leaf color* (*upper surface*).—Green 137A with 3 to 6 yellow-green center stripes that vary from 144B to 154B to 154D along the length of the leaf that are 1 mm to 4 mm wide and margins grey-red 186C that are 1.5 mm wide.
*Vein color* (*lower surface*).—182A.
*Vein color* (*upper surface*).—195B.
*Leaf attachment.*—Sessile.
*Durability of foliage to stress.*—High.
Flower: Flowering has not been observed.
Disease resistance: 'Norjim' has good resistance during the rainy season to bacterial growth.

It is claimed:

1. A new and distinct variety of *Dracaena* plant named 'Norjim' as described and illustrated.

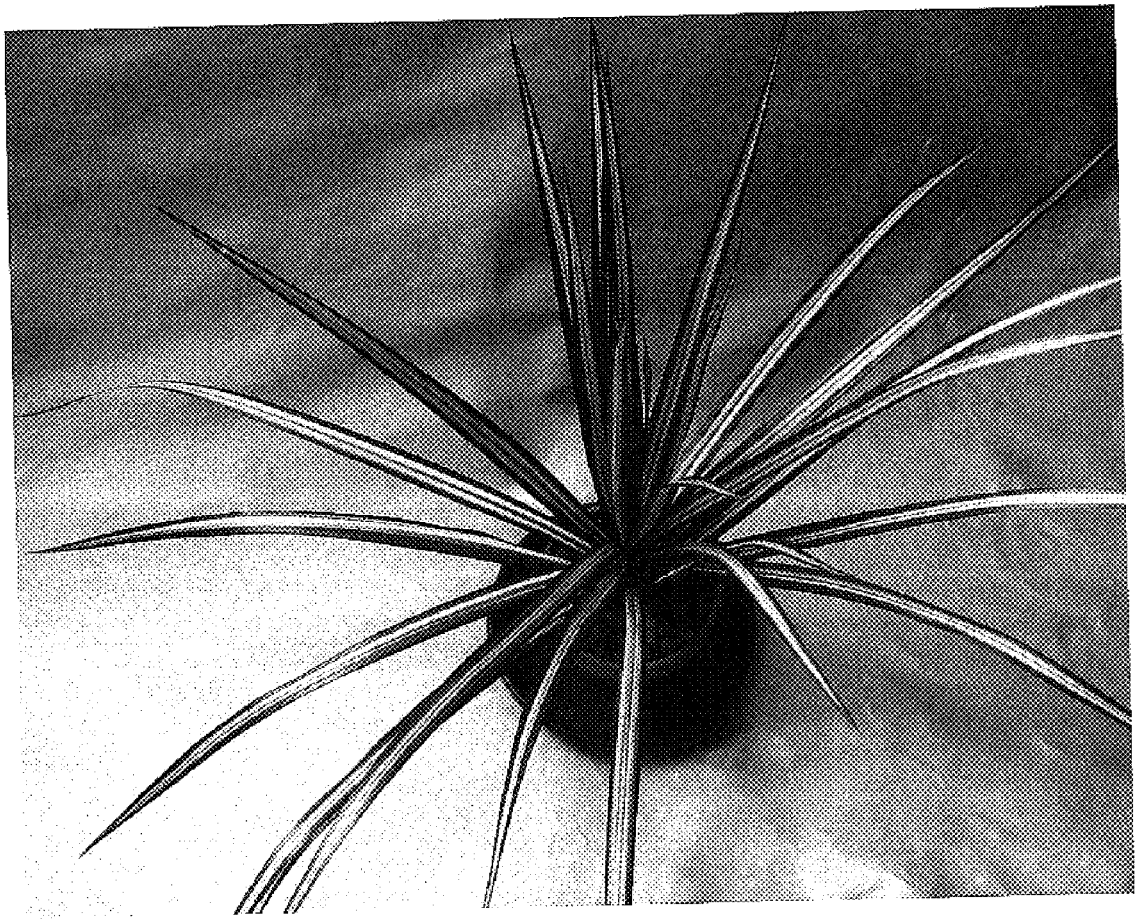

* * * * *